(12) United States Patent
Wright et al.

(10) Patent No.: US 7,626,043 B2
(45) Date of Patent: Dec. 1, 2009

(54) ANTIPROLIFERATIVE ACTIVITY OF THE LEIODERMATOLIDE CLASS OF MACROLIDES

(75) Inventors: Amy E. Wright, Fort Pierce, FL (US); John K. Reed, Fort Pierce, FL (US); Jill Roberts, Vero Beach, FL (US); Ross E. Longley, Tallahassee, FL (US)

(73) Assignee: Florida Atlantic University Board of Trustees, Boca Raton, FL (US)

( * ) Notice: Subject to any disclaimer, the term of this patent is extended or adjusted under 35 U.S.C. 154(b) by 32 days.

(21) Appl. No.: 11/890,686

(22) Filed: Aug. 6, 2007

(65) Prior Publication Data

US 2008/0033035 A1 Feb. 7, 2008

Related U.S. Application Data

(60) Provisional application No. 60/835,639, filed on Aug. 4, 2006.

(51) Int. Cl.
*C07D 313/04* (2006.01)
*A01N 43/02* (2006.01)

(52) U.S. Cl. ...................... 549/271; 514/450
(58) Field of Classification Search .............. 549/271; 514/450
See application file for complete search history.

(56) References Cited

U.S. PATENT DOCUMENTS 5,430,053 A 7/1995 Pettit et al.

OTHER PUBLICATIONS

Gunasekera, S. P. et al., "Discodermolide: A New Bioactive Polyhydroxylated Lactone from the Marine Sponge *Discodermia dissoluta*," *Journal of Organic Chemistry*, 1990, Vol. 55, No. 16, pp. 4912-4915.
Pisera, A. et al., "Family Azoricidae Sollas, 1888," *Systema Porifera: A Guide to the Classification of Sponges*, 2002, pp. 352-355.
Van Soest, R. W. M. et al., "Barbados Deep-Water Sponges," *Studies on the Fauna of Curaçao and Other Caribbean Islands*: No. 215, 1988, pp. 1-175.

*Primary Examiner*—D. Margaret Seaman
*Assistant Examiner*—Nizal S Chandrakumar
(74) *Attorney, Agent, or Firm*—Saliwanchik, Lloyd & Saliwanchik

(57) ABSTRACT

The subject invention provides novel biologically active compounds that have utility for use in inhibiting cellular proliferation. Pharmaceutical compositions comprising these compounds are also provided. In a specific embodiment, the compounds and compositions of the subject invention can be used in the treatment of cancer.

3 Claims, 3 Drawing Sheets

ANTIPROLIFERATIVE ACTIVITY OF THE LEIODERMATOLIDE CLASS OF MACROLIDES

CROSS-REFERENCE TO A RELATED APPLICATION

This application claims the benefit of U.S. provisional application Ser. No. 60/835,639, filed Aug. 4, 2006, which is hereby incorporated by reference in its entirety.

GOVERNMENT SUPPORT

This invention was made with government support under a grant awarded from the National Institute of Health/National Cancer Institute under grant number 1RO1-CA-093455. The government has certain rights in the invention.

FIELD OF THE INVENTION

This invention relates to organic compounds and compositions that have useful therapeutic properties. More particularly, the invention provides novel macrolide compounds having anti-proliferative and antitumor activities, pharmaceutical compositions comprising such compounds, and methods of their use for therapeutic purposes.

BACKGROUND OF THE INVENTION

Of great importance to man is the control of pathological cellular proliferation such as that which occurs in the case of cancer. Considerable research and resources have been devoted to oncology and antitumor measures including chemotherapy. While certain methods and chemical compositions have been developed which aid in inhibiting, remitting, or controlling the growth of, for example, tumors, new methods and antitumor chemical compositions are needed. Antiproliferative agents can also be useful in treating autoimmune diseases and inflammatory disease.

In searching for new biologically active compounds, it has been found that some natural products and organisms are potential sources for chemical molecules having useful biological activity of great diversity. For example, the diterpene commonly known as paclitaxel, isolated from several species of yew trees, is a mitotic spindle poison that stabilizes microtubules and inhibits their depolymerization to free tubulin (Fuchs, D. A., R. K. Johnson (1978) *Cancer Treat. Rep.* 62:1219-1222; Schiff, P. B., J. Fant, S. B. Horwitz (1979) *Nature* (London) 22:665-667). Paclitaxel is also known to have antitumor activity and has undergone a number of clinical trials which have shown it to be effective in the treatment of a wide range of cancers (Rowinski, E. K. R. C. Donehower (1995) *N. Engl. J. Med.* 332:1004-1014). See also, e.g., U.S. Pat. Nos. 5,157,049; 4,960,790; and 4,206,221.

Marine sponges have also proven to be a source of biologically active chemical molecules. A number of publications disclose organic compounds derived from marine sponges including Scheuer, P. J. (ed.) *Marine Natural Products, Chemical and Biological Perspectives*, Academic Press, New York, 1978-1983, Vol. I-V; Uemura, D., K. Takahashi, T. Yamamoto, C. Katayama, J. Tanaka, Y. Okumura, Y. Hirata (1985) *J. Am. Chem. Soc.* 107:4796-4798; Minale, L. et al. (1976) *Fortschr. Chem. org. Naturst.* 33:1-72 Faulkner, D. J., *Nat. Prod. Reports* 1984, 1, 251-551; ibid. 1987, 4, 539; ibid 1990, 7, 269; ibid 1993, 10, 497; ibid 1994, 11, 355; ibid 1995, 12, 22; ibid 1998, 15:113-58; ibid 2000 17:1-6; ibid 2000 17: 7-55; ibid 2001, 18: 1-49; 2002, 19: 1-48; Gunasekera, S. P., M. Gunasekera, R. E. Longley and G. K. Schulte (1990) *J. Org. Chem.*, 55:4912-4915; Horton, P. A., F. E. Koehn, R. E. Longley, and O. J. McConnell, (1994) *J. Am. Chem. Soc.* 116: 6015-6016.

BRIEF SUMMARY

The subject invention provides novel biologically active compounds that have utility for inhibiting pathological cellular proliferation. Pharmaceutical compositions comprising these compounds are also provided. In a specific embodiment, the compounds and compositions of the subject invention can be used in the treatment of cancer.

In one embodiment, the novel compositions and methods of the subject invention can be used in the treatment of an animal hosting cancer cells including, for example, inhibiting the growth of tumor cells in a mammalian host. More particularly, the subject compounds can be used for inhibiting in a human the growth of tumor cells, including cells of breast, colon, CNS, ovarian, renal, prostate, liver, pancreatic, uterine, or lung tumors, as well as human leukemia or melanoma cells.

The mechanisms for achieving anticancer activity exhibited by the subject compounds would lead a person of ordinary skill in the art to recognize the applicability of the subject compounds, compositions, and methods to additional types of cancer as described herein.

In accordance with the subject invention, methods for inhibiting cancer cells in a host include contacting tumor cells with an effective amount of the new pharmaceutical compositions of the invention. The cancer cells inhibited by the invention are those which are susceptible to the subject compounds described herein or compositions comprising those compounds.

In one embodiment, the subject invention provides compounds having the following structural formula:

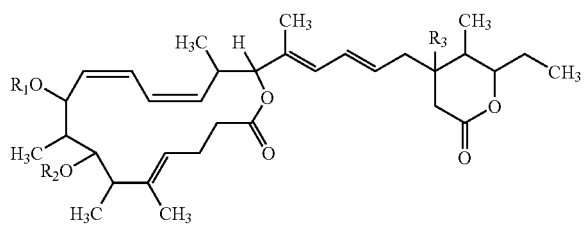

wherein $R_1$=—H, -A, —$CH_2$-Q, —COA, COZ or CONXY;

$R_2$=—H, -A, —$CH_2$-Q, —COA, COZ or CONXY;

$R_3$=—H, —OH or -A;

A=lower alkyl;

Z=monocyclicaryl;

Q=phenyl, tolyl or xylyl;

X=—H-A, -Z or —$CH_2$-Z; and and Y=—H, -A, -Z, —$CH_2$-Z, or —COA, —COZ, or a salt thereof.

In a specific embodiment, the subject invention provides leiodermatolide, which has the following structure:

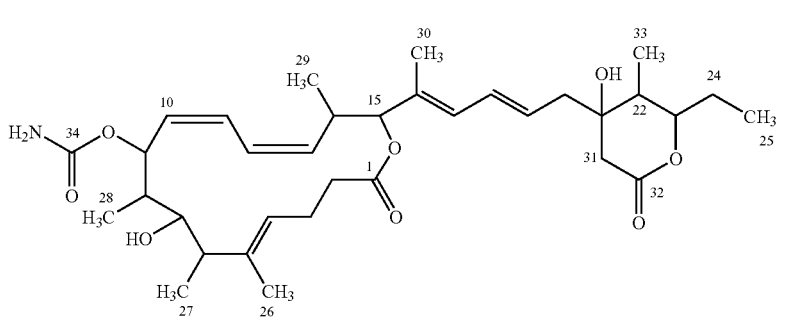

Leiodermatolide is a novel composition which inhibits the proliferation of cancer cells. As described herein, it causes a G2/M block in the cell cycle. It can be isolated from a deep-water sponge of the genus *Leiodermatium* collected in the US and Bahamas.

Additional aspects of the invention include the provision of methods for producing the new compounds and compositions.

Other objects and further scope of applicability of the present invention will become apparent from the detailed descriptions given herein; it should be understood, however, that the detailed descriptions, while indicating preferred embodiments of the invention, are given by way of illustration only, since various changes and modifications within the spirit and scope of the invention will become apparent from such descriptions.

BRIEF DESCRIPTION OF THE DRAWINGS

The file of this patent application contains at least one drawing executed in color. Copies of this patent or patent application publication with color drawings(s) will be provided by the Patent and Trademark Office upon request and payment of the necessary fee.

DETAILED DISCLOSURE

Figure 1:
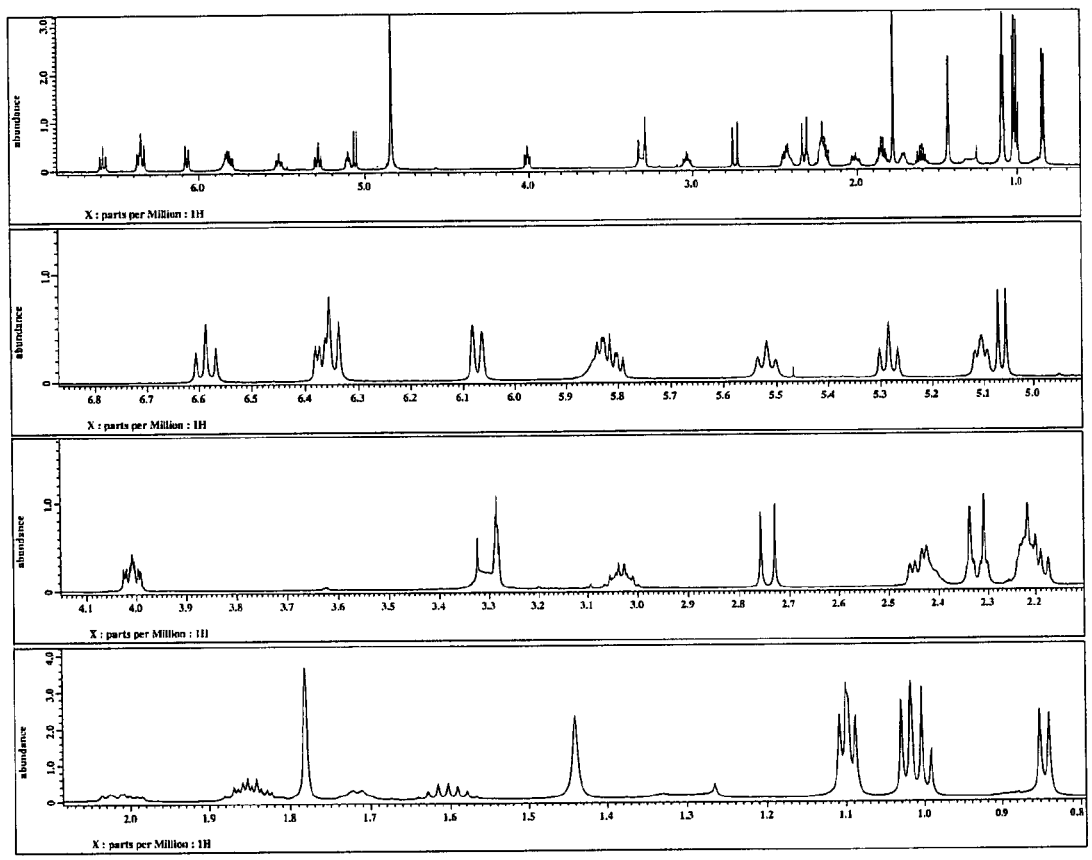
FIG. 1 $^1$H NMR Spectrum of Leiodermatolide (d4-Methanol 600 MHz) referenced to methanol at 3.31 ppm.
Figure 2:
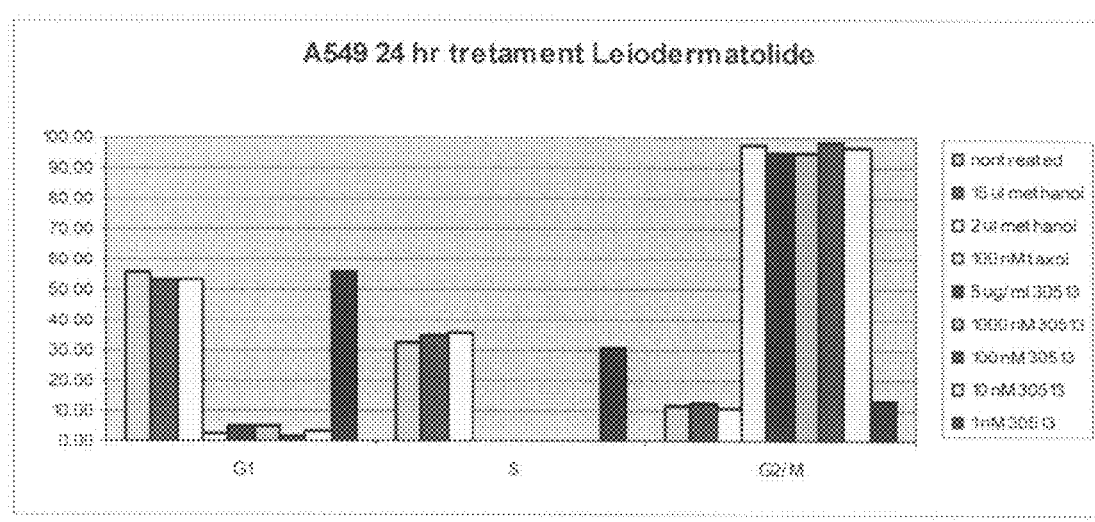
FIG. 2 Graphical representation of leiodermatolide in Cell Cycle Analysis using the A549 cell line.
Figure 3:
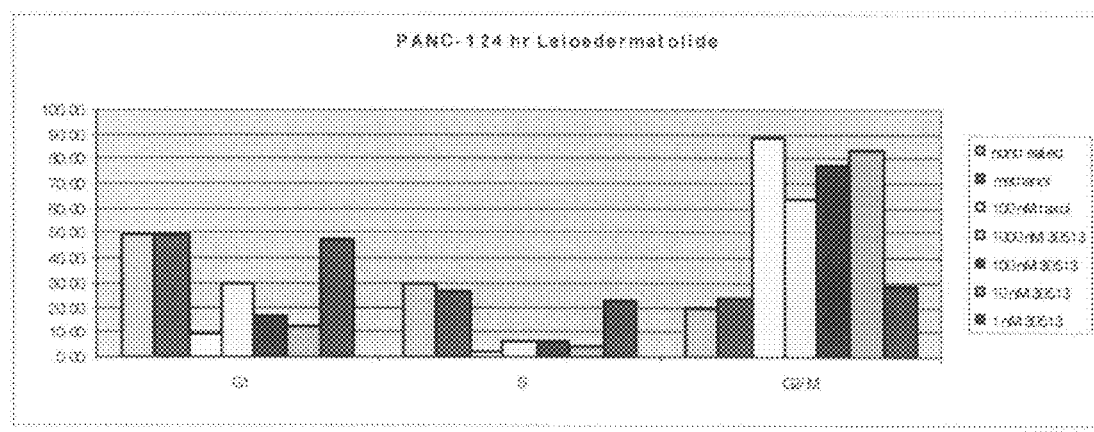
FIG. 3 Graphical representation of leiodermatolide in Cell Cycle Analysis using the PANC-1 pancreatic carcinoma cell line.

The subject invention provides novel biologically active compounds that are useful in inhibiting cellular proliferation. Pharmaceutical compositions comprising these compounds are also provided. In a specific embodiment, the compounds and compositions of the subject invention can be used in the treatment of tumors and other forms of cancer.

In one embodiment, the novel compositions and methods of the subject invention can be used in the treatment of an animal hosting cancer cells including, for example, inhibiting the growth of tumor cells in a mammalian host. More particularly, the subject compounds can be used for inhibiting in a human the growth of tumor cells, including cells of breast, colon, CNS, ovarian, renal, prostate, liver, pancreatic, uterine, or lung tumors, as well as human leukemia or melanoma cells. Advantageously, the compounds of the subject invention can be used to treat multidrug resistant cancers.

One aspect of the present invention is an extract from the sponge *Leiodermatium* sp., which showed potent inhibition of mitosis in the Phosphonucleolin Cytoblot Assay. Bioassay-guided fractionation led to the purification of an active fraction with potent cytotoxic activity against a panel of human tumor cell lines. As described herein, structure elucidation was accomplished through the use of spectroscopic techniques.

Leiodermatolide is a novel composition that causes a G2/M block in the cell cycle. As described herein, it can be isolated from a deep-water sponge of the genus *Leiodermatium* collected in the US and Bahamas.

The mechanisms for achieving anticancer activity exhibited by the subject compounds would lead a person of ordinary skill in the art to recognize the applicability of the subject compounds, compositions, and methods to additional types of cancer as described herein.

In accordance with the subject invention, methods for inhibiting cancer cells in a host include contacting tumor cells with an effective amount of the new pharmaceutical compositions of the invention. The cancer cells inhibited by the invention are those which are susceptible to the subject compounds described herein or compositions comprising those compounds.

In one embodiment, the subject invention provides compounds having the following structural formula:

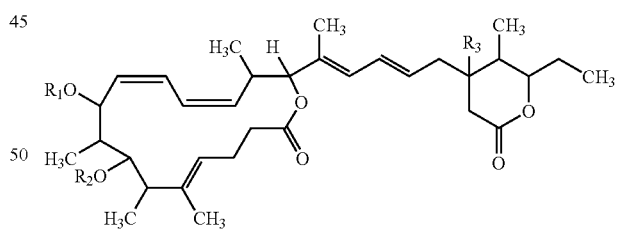

wherein
$R_1$=—H, -A, —$CH_2$-Q, —COA, COZ or CONXY;
$R_2$=—H, -A, —$CH_2$-Q, —COA, COZ or CONXY;
$R_3$=—H, —OH or -A;
A=lower alkyl;
Z=monocyclicaryl;
Q=phenyl, tolyl or xylyl;
X=—H-A, -Z or —$CH_2$-Z; and
and Y=—H, -A, -Z, —$CH_2$-Z, or —COA, —COZ, or a salt thereof.

In a specific embodiment, the subject invention provides leiodermatolide and analogs thereof. Leiodermatolide has the following structure:

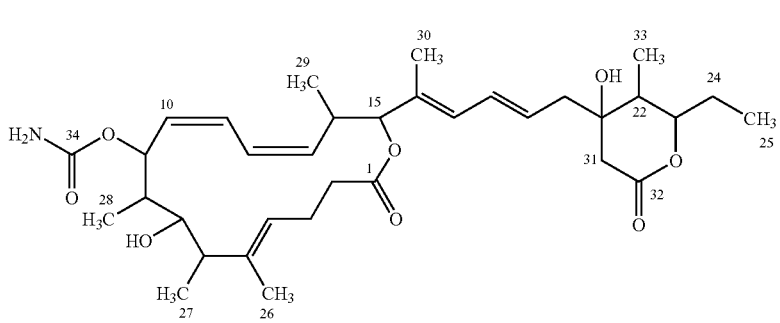

As used in this application, the term "analogs" refer to compounds that are substantially the same as another compound but which may have been modified by, for example, adding side groups, oxidation or reduction of the parent structure. Salts are also within the scope of the present invention. Analogs or derivatives of the exemplified compounds can be readily prepared using commonly known standard reactions. These standard reactions include, but are not limited to, hydrogenation, alkylation, acetylation, and acidification reactions.

In further embodiments of the invention, salts within the scope of the invention are made by adding mineral acids, e.g., HCl, $H_2SO_4$, or strong organic acids, e.g., formic, oxalic, in appropriate amounts to form the acid addition salt of the parent compound or its derivative. Also, synthesis type reactions may be used pursuant to known procedures to add or modify various groups in the preferred compounds to produce other compounds within the scope of the invention.

The examples which follow are not meant to be fully inclusive of all methods which could be used to purify the subject compounds, but rather should be taken as examples of methods which can be used. A scientist skilled in the art of natural products purification could build upon the methods described and substitute a variety of solvents and stationary phases for those described in the preferred embodiment of the invention. In addition to chromatography, methods such as crystallization and partitioning could also be used to purify the desired compounds.

Following are examples which illustrate procedures for practicing the invention. These examples should not be construed as limiting. All percentages are by weight and all solvent mixture proportions are by volume unless otherwise noted.

EXAMPLE 1

Collection of Sponge Source Material

This 'lithistid' demosponge specimen was collected using Harbor Branch Oceanographic Institution's Johnson-Sea-Link research submersible on the Miami Terrace in the Straits of Florida, 26° 01.277' N latitude and 79° 49.266' W longitude, from a steep rocky slope and at a depth of 401 m. A large voucher specimen is deposited at the Harbor Branch Oceanographic Museum for the following specimen: BMR # 1-VI-04-2-005, Taxonomy—*Leiodermatium* sp. and the HBO Museum Catalog Number is 003:01035.

Taxonomic diagnosis and description: *Leiodermatium* Schmidt, 1870, unidentified species (Phylum—Porifera, Class—Demospongiae, ('lithistida'), Family—Azoricidae). The former order 'Lithistida' is a polyphyletic group characterized by choanosomal articulated spicules called desmas that form a rigid skeleton. The genus is described as foliated to vase to ear-shaped in habit; one surface with large elevated oscules, the other with small pores; desmas strongly spinose rhizoclones; no special ectosomal spicules; no microscleres; and accessory megascleres are large oxeas (Pisera and Levi, 2002). The genus has been included into various families including Leiodermatidae and Siphonidiidae. According to Pisera and Levi (2002), the paucity of characters makes species differentiation and determination difficult, and the genus badly needs revision. This particular specimen fits the description of the genus and is described as a foliated, rippling plate, ~25 cm diameter. The plate is ~4 mm thick, very hard consistency, and is tan in color. The convex side is relatively smooth and the inner side has small raised pores. The choanosomal skeleton consists of rhizoclone desmas which are strongly branched and the tips are divided into fine spiny processes. No microscleres are apparent, although some 200-350 micron oxeas are present; Van Soest and Stentoft (1988) also reported accessory oxeas in material from Barbados.

Pisera, Andrzej and Claude Levi. 2002. Family Azoricidae Sollas, 1888. Pages 352-355, in John N. A. Hooper, Rob W. M. Van Soest (editors), Systema Profera. A Guide to the Classification of Sponges, Volume 1, Kluwer Academic, Plenum Publishers, NY. Soest, R. W. M. Van and N. Stentoft. 1988. Barbados Deep-Water Sponges. In P. W. Hummelinck and L. J. Van der Steen (editors), Uitgaven van de Natuurwetenschappelijke Studiekring voor Suriname en de Nederlandse Antillen. No. 122. Studies on the Fauna of Curacao and other Caribbean Islands 70(215): 1-175.

EXAMPLE 2

Isolation of the Leiodermatolide Class of Natural Products

One thousand and thirty-seven (1037) grams of the frozen *Leiodermatium* sponge, 1-VI-04-2-005 was extracted exhaustively by macerating with ethyl acetate:\ethanol (9:1 v/v) using a Waring Blender (10×250 mL). The combined filtered extracts were concentrated by distillation under reduced pressure to yield 20.13 g of crude residue. The residue was partitioned between ethyl acetate and water (5×250 ml portions).

After concentration, the ethyl acetate phase (2.89 g) was chromatographed under vacuum column chromatographic conditions on a Kieselgel 60H (EM SCIENCE) stationary phase. A 150 mL Buchner funnel fitted with a medium porosity fritted glass disc was used as the column. The stationary phase was packed to a total height of 4 cm. The ethyl acetate partition was applied as a slurry to the column in a mixture of heptane-ethyl acetate (8:2 v/v). Fractions were eluted using a 20% step gradient of ethyl acetate in heptane followed by a series of fractions containing increasing amounts of methanol in ethyl acetate [Fraction 1: heptane-ethyl acetate 80:20 v/v (200 ml) Fraction 2: heptane-ethyl acetate 60:40 v/v (200 ml); fraction 3: heptane-ethyl acetate 40:60 v/v (200 ml); fraction 4: heptane-ethyl acetate 20:80 v/v (200 ml); fraction 5: 100% ethyl acetate (200 ml); fraction 6: ethyl acetate-methanol 75:25 v/v (200 ml); Fraction 7: ethyl acetate-methanol 50:50 v/v (200 ml); Fraction 8 ethyl acetate-methanol 25:75 v/v (200 ml); Fraction 9: methanol (200 ml). Leiodermatolide eluted cleanly into fraction 4. Fraction 4 was further separated by HPLC using a Vydac C-18 Protein and Peptide Column (10 mm×250 mm, 10μ particle size), flow rate=3 ml/min; a gradient elution was used s follows: Solvent A: Water:acetonitrile 95:5 v/v; Solvent B: acetonitrile; t=0 A:B 4:6 v/v; t=13 minutes A:B 25:75 v/v; t=18 minutes 100% B; hold for 5 minutes at 100% B. The separation was monitored by UV at 230 nm. Leiodermatolide elutes after approximately 6.8 column volumes under these conditions.

Leiodermatolide (I):white powder; MS:M+H$^+$ m/z observed 601, See Table 1 for $^1$H and $^{13}$C NMR data. The proton NMR spectrum is shown in FIG. 1.

TABLE 1

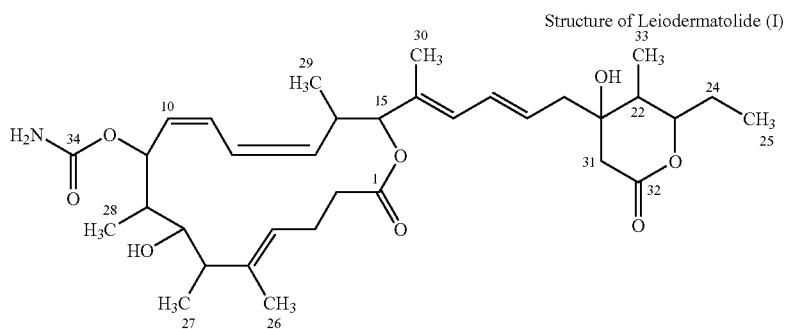

Structure of Leiodermatolide (I)

NMR Data for Leiodermatolide

| Atom # | $\delta_C$ | C multiplicity | | $\delta_H$ | multiplicity | J (hz) |
|---|---|---|---|---|---|---|
| 1 | 173.91 | C | | | | |
| 2 | 34.56 | CH2 | A | 2.33 | m | |
| | | | B | 2.03 | m | |
| 3 | 22.97 | CH2 | | 2.22 | m | |
| 4 | 126.40 | CH broad | | 5.10 | dd | 6.9, 6.9 |
| 5 | 137.68 | C | | | | |
| 6 | 49.41 | CH (hidden) | | 2.42 | bs | |
| 7 | 80.31 | CH broad | | 3.31 | bm | |
| 8 | 40.84 | CH broad | | 1.72 | bq | 6.8 |
| 9 | 69.67 | CH broad | | 5.84 | bd | 13.7 |
| 10 | 130.23 | CH | | 5.51 | dd | 10.3, 10.3 |
| 11 | 126.40 | CH broad | | 6.36 | dd | 12.3, 11.7 |
| 12 | 125.82 | CH | | 6.58 | dd | 11.3, 11.3 |
| 13 | 137.97 | CH | | 5.28 | dd | 10.3, 10.3 |
| 14 | 35.74 | CH | | 3.03 | bm | |
| 15 | 84.38 | CH | | 5.05 | d | 10.3 |
| 16 | 133.45 | C | | | | |
| 17 | 131.37 | CH | | 6.07 | d | 10.3 |
| 18 | 130.85 | CH | | 6.35 | dd | 11.0, 11.0 |
| 19 | 131.06 | CH | | 5.81 | ddd | 15.2, 8.1, 6.2 |
| 20 | 39.40 | CH2 | a | 2.43 | dd | 14.5, 3 |
| 20 | | | b | 2.19 | dd | 14.5, 11.7 |
| 21 | 72.73 | C | | | | |
| 22 | 44.63 | CH | | 1.85 | dq | 9.6, 7.6 |
| 23 | 85.56 | CH | | 4.01 | ddd | 10.3, 7.6, 2.8 |
| 24 | 27.92 | CH2 | a | 1.84 | m | |
| 24 | | | b | 1.61 | ddt | 14.4, 6.8, 6.8 |
| 25 | 9.42 | CH3 | | 1.00 | t | 7.4 |
| 26 | 11.54 | CH3 | | 1.44 | bs | |
| 27 | 16.92 | CH3 | | 1.10 | d | 6.5 |
| 28 | 12.94 | CH3 | | 1.08 | d | 7.2 |
| 29 | 16.92 | CH3 | | 0.86 | d | 6.7 |
| 30 | 11.89 | CH3 | | 1.78 | s | |
| 31 | 43.16 | CH2 | a | 2.72 | d | 17.2 |
| 31 | | | b | 2.31 | d | 17.2 |
| 32 | 173.63 | C | | | | |
| 33 | 11.54 | CH3 | | 1.02 | d | 6.9 |
| 34 | 159.97 | C | | | | |

EXAMPLE 3

Cytotoxicity of Leiodermatolide to Cancer Cells

Leiodermatolide was analyzed as to its effects on the proliferation of a panel of tumor cell lines including both cell lines. The cell lines tested include: A549 human lung adenocarcinoma, NCI-ADR-RES (Formerly MCF-7/ADR) human cancer, PANC-1 human pancreatic cancer, DLD-1 human colorectal carcinoma, and P388 murine leukemia cell lines. P388 cells were obtained from Dr. R. Camalier, National Cancer Institute Bethesda, Md., and A549, PANC-1, DLD-1 and NCI-ADR-RES cells were obtained from American Type Culture Collection, Rockville, Md. The A549, NCI-ADR-RES, PANC-1, DLD-1 and P388 cell lines are maintained in Roswell Park Memorial Institute (RPMI) medium 1640 supplemented with 100 U/mL penicillin 100 µg/ml streptomycin, 60 µg/ml L-glutamine, 18 mM HEPES, 0.05 mg/mL gentamycin and 10% fetal bovine serum (for the PANC-1, and DLD-1 cell lines the media is also supplemented with 100 µg/ml sodium pyruvate and 2.5 mg/ml glucose).

Cell lines are cultured in plastic tissue culture flasks and kept in an incubator at 37° C. in humidified air containing 5% $CO_2$.

To assess the antiproliferative effects of agents against the various cell lines, 200 µl cultures (96-well tissue culture plates, Nunc, Denmark) are first established at $3\times10^4$ cells/ml for adherent lines (A549, NCl ADR-RES, PANC-1, and DLD-1) and $1\times10^5$ for non-adherent lines (P388) in tissue culture medium and incubated for 24 hr at 37° C. in 10% $CO_2$ in air in order to allow cells to attach. A volume of 100 µl of medium is removed from each test well and 100 µl of medium containing serial, two-fold dilutions of the test agent is added to each well containing tumor cells. Medium without drug is also added to wells containing tumor cells which serve as no drug controls. Positive drug controls are included to monitor drug sensitivity of each of the cell lines. These include varying dilutions of 5-fluorouracil and doxorubicin. After 72-h exposures (Adherent cell lines) or 48-hr exposure (Non-adherent cell lines), tumor cells are enumerated using 3-[4,5-Dimethylthiazol-2-yl]-2,5-diphenyltetrazolium bromide (MTT) (M. C. Alley, et al., Cancer Res. 48:589, 1988) as follows:

A volume of 75 µl of warm growth media containing 5 mg/ml MTT is added to each well, cultures returned to the incubator, and left undisturbed for 3 hours. To spectrophotometrically quantitate formation of reduced formazan, plates are centrifuged (900×g, 5 minutes), culture fluids removed by aspiration, and 200 µl of acidified isopropanol (2 ml concentrated HCl/liter isopropanol) added per well. The absorbance of the resulting solutions is measured at 570 nm with a plate reader (BMG labtech NOVOStar). The absorbance of tests wells is divided by the absorbance of drug-free wells, and the concentration of agent that results in 50% of the absorbance of untreated cultures ($IC_{50}$) is determined by linear regression of logit-transformed data (D. J. Finney, Statistical Method in Biological Assay, third ed., pp. 316-348, Charles Griffin Co., London, 1978). A linear relationship between tumor cell number and formazan production has been routinely observed over the range of cell densities observed in these experiments. The two standard drug controls (indicated above) are included in each assay to monitor the drug sensitivity of each of the cell lines and $IC_{50}$ values are determined for each drug-cell combination.

A summary of results in these assays for compound I can be found in Table 2.

TABLE 2

Cytotoxicity Results for Leiodermatolide

| | A549 $IC_{50}$ | NCIADR-RES $IC_{50}$ | P388 $IC_{50}$ | PANC-1 $IC_{50}$ | DLD-1 $IC_{50}$ |
|---|---|---|---|---|---|
| Leiodermatolide (I) | 3.3 nM | 233 nM | 3.3 nM | 5.0 nM | 8.3 nM |

EXAMPLE 4

Effect of Leiodermatolide on Cell Cycle Progression of A549 Human Lung Adenocarcinoma Cells in Comparison to Paclitaxel A549 human lung adenocarcinoma cells were used as cell cycle targets to compare the effects on perturbation of the cell cycle of leiodermatolide to the known mitotic spindle inhibitor Paclitaxel. Cell cycle analyses were performed as follows: A549 human lung adenocarcinoma cells were incubated in tissue culture media (TCM=Roswell Park Memorial Institute (RPMI) medium 1640 supplemented with 100 U/ml penicillin, 100 mg/ml streptomycin, 60 mg/ml 1-glutamine, 18 mM HEPES, 0.05 mg/ml gentamicin and 10% fetal bovine serum) at 37° C. in 5% $CO_2$ in air in the presence or absence of varying concentrations of leiodermatolide or Paclitaxel for 24 hours.

Cells were harvested, fixed in ethanol and stained with 0.02 mg/ml of propidium iodide (P.I.) together with 0.1 mg/ml of RNAse A. This procedure permeabilizes cells and allows entry of P.I. to stain DNA (propidium iodide also stains double stranded RNA, so RNAse is included in the preparation to exclude this possibility). Stained preparations were analyzed on a BD Sciences Calibur Flow Cytometer with 488 nm excitation. Fluorescence measurements and resulting DNA histograms were collected from at least 3,000 P.I. stained cells at an emission wavelength of 690 nM. Raw histogram data was further analyzed using a cell cycle analysis program (Multicycle, Phoenix Flow Systems).

The results of these experiments are shown in Table 3. Non-treated control A549 cells exhibited a typical pattern of cell cycling, with a large percentage (55%) of the cell population comprising the $G_1$ population (first peak) with lesser percentages comprising both the S (32%) and $G_2/M$ (12%) phases of the cell cycle. A549 cells treated with 100 nM Paclitaxel exhibited decreased percentages of cells comprising the $G_1$ population (2%) and S populations (0%) and a corresponding increased percentage in the $G_2/M$ (98%) phase of the cell cycle indicating Paclitaxel's ability to induce $G_2/M$ block. A549 cells treated with 100 nM leiodermatolide exhibited decreased percentages of cells comprising the $G_1$ population (2%) and S populations (0%) and a corresponding increased percentage in the $G_2/M$ (98%) phase of the cell cycle indicating leiodermatolide's ability to induce $G_2/M$ block. A549 cells treated with 10 nM leiodermatolide exhibited decreased percentages of cells comprising the $G_1$ population (3%) and S populations (0%) and a corresponding increased percentage in the $G_2/M$ (97%) phase of the cell cycle indicating leiodermatolide's ability to induce $G_2/M$ block.

TABLE 3

Cell Cycle Analysis results for Leiodermatolide
in the A549 lung carcinoma cell line

|  |  | G1 | S | G2/M |
|---|---|---|---|---|
| A549 24 hr | nontreated | 55.45 | 32.47 | 12.08 |
|  | 15 ul methanol | 53.10 | 34.69 | 12.22 |
|  | 2 ul methanol | 53.17 | 36.23 | 10.60 |
|  | 100 nM taxol | 2.18 | 0.00 | 97.82 |
|  | 1000 nM Leiodermatolide | 4.99 | 0.00 | 95.01 |
|  | 100 nM Leiodermatolide | 1.70 | 0.00 | 98.30 |
|  | 10 nM Leiodermatolide | 2.97 | 0.00 | 97.03 |
|  | 1 nM Leiodermatolide | 55.75 | 30.85 | 13.40 |

EXAMPLE 5

Effect of Leiodermatolide on Cell Cycle Progression of PANC-1 Human Pancreatic Carcinoma Cells in Comparison to Paclitaxel PANC-1 human pancreatic carcinoma cells were used as cell cycle targets to compare the effects on perturbation of the cell cycle of leiodermatolide and the known mitotic spindle inhibitor Paclitaxel. Cell cycle analyses were performed as follows: PANC-1 human lung adenocarcinoma cells were incubated in tissue culture media (TCM=Roswell Park Memorial Institute (RPMI) medium 1640 supplemented with 100 U/ml penicillin, 100 mg/ml streptomycin, 60 mg/ml 1-glutamine, 18 mM HEPES, 0.05 mg/ml gentamicin, 100 µg/ml sodium pyruvate, 2.5 mg/ml glucose and 10% fetal bovine serum) at 37° C. in 5% $CO_2$ in air in the presence or absence of varying concentrations of leiodermatolide or Paclitaxel for 24 hours.

Cells were harvested, fixed in ethanol and stained with 0.02 mg/ml of propidium iodide (P.I.) together with 0.1 mg/ml of RNAse A. This procedure permeabilizes cells and allows entry of P.I. to stain DNA (propidium iodide also stains double stranded RNA, so RNAse is included in the preparation to exclude this possibility). Stained preparations were analyzed on a BD Sciences Calibur Flow Cytometer with 488 nm excitation. Fluorescence measurements and resulting DNA histograms were collected from at least 3,000 P.I. stained cells at an emission wavelength of 690 nM. Raw histogram data was further analyzed using a cell cycle analysis program (Multicycle, Phoenix Flow Systems).

The results of these experiments are shown in Table 4. Non-treated control PANC-1 cells exhibited a typical pattern of cell cycling, with a large percentage (49%) of the cell population comprising the G1 population (first peak) with lesser percentages comprising both the S (30%) and G2/M (20%) phases of the cell cycle. PANC-1 cells treated with 100 nM Paclitaxel exhibited decreased percentages of cells comprising the G1 population (10%) and S populations (2%) and a corresponding increased percentage in the G2/M (88%) phase of the cell cycle indicating Paclitaxel's ability to induce G2/M block. PANC-1 cells treated with 100 nM leiodermatolide exhibited decreased percentages of cells comprising the G1 population (16%) and S populations (6%) and a corresponding increased percentage in the G2/M (77%) phase of the cell cycle indicating leiodermatolide's ability to induce G2/M block. PANC-1 cells treated with 10 nM leiodermatolide exhibited decreased percentages of cells comprising the G1 population (12%) and S populations (4%) and a corresponding increased percentage in the G2/M (83%) phase of the cell cycle indicating leiodermatolide's ability to induce G2/M block.

TABLE 4

Cell Cycle Analysis results for Leiodermatolide
in the PANC-1 pancreatic carcinoma cell line

|  |  | G1 | S | G2/M |
|---|---|---|---|---|
| PANC-1 24 hr | nontreated | 49.55 | 30.41 | 20.04 |
|  | methanol | 49.99 | 26.65 | 23.36 |
|  | 100 nM paclitaxel | 9.76 | 1.88 | 88.36 |
|  | 1000 nM Leiodermatolide | 29.54 | 6.53 | 63.92 |
|  | 100 nM Leiodermatolide | 16.55 | 6.00 | 77.45 |
|  | 10 nM Leiodermatolide | 12.04 | 4.51 | 83.45 |
|  | 1 nM Leiodermatolide | 47.88 | 23.18 | 28.93 |

EXAMPLE 6

Formulation and Administration

The compounds of the invention are useful for various non-therapeutic and therapeutic purposes. It is apparent from the testing that the compounds of the invention are effective for inhibiting cell growth. Because of the antiproliferative properties of the compounds, they are useful to prevent unwanted cell growth in a wide variety of settings including in vitro uses. They are also useful as standards and for teaching demonstrations. They can also be used as ultraviolet screeners in the plastics industry since they effectively absorb UV rays. As disclosed herein, they are also useful prophylactically and therapeutically for treating cancer cells in animals and humans.

Therapeutic application of the new compounds and compositions containing them can be accomplished by any suitable therapeutic method and technique presently or prospectively known to those skilled in the art. Further, the compounds of the invention have use as starting materials or intermediates for the preparation of other useful compounds and compositions.

The dosage administration to a host in the above indications will be dependent upon the identity of the cancer cells, the type of host involved, its age, weight, health, kind of concurrent treatment, if any, frequency of treatment, and therapeutic ratio.

The compounds of the subject invention can be formulated according to known methods for preparing pharmaceutically useful compositions. Formulations are described in detail in a number of sources which are well known and readily available to those skilled in the art. For example, Remington's Pharmaceutical Science by E. W. Martin describes formulations which can be used in connection with the subject invention. In general, the compositions of the subject invention will be formulated such that an effective amount of the bioactive compound(s) is combined with a suitable carrier in order to facilitate effective administration of the composition.

In accordance with the invention, pharmaceutical compositions comprising, as an active ingredient, an effective amount of one or more of the new compounds and one or more non-toxic, pharmaceutically acceptable carrier or diluent. Examples of such carriers for use in the invention include ethanol, dimethyl sulfoxide, glycerol, silica, alumina, starch, and equivalent carriers and diluents.

To provide for the administration of such dosages for the desired therapeutic treatment, new pharmaceutical compositions of the invention will advantageously comprise between about 0.1% and 45%, and especially, 1 and 15%, by weight of the total of one or more of the new compounds based on the weight of the total composition including carrier or diluent. Illustratively, dosage levels of the administered active ingredients can be: intravenous, 0.01 to about 20 mg/kg; intraperitoneal, 0.01 to about 100 mg/kg; subcutaneous, 0.01 to about 100 mg/kg; intramuscular, 0.01 to about 100 mg/kg; orally 0.01 to about 200 mg/kg, and preferably about 1 to 100 mg/kg; intranasal instillation, 0.01 to about 20 mg/kg; and aerosol, 0.01 to about 20 mg/kg of animal (body) weight.

It should be understood that the examples and embodiments described herein are for illustrative purposes only and that various modifications or changes in light thereof will be suggested to persons skilled in the art and are to be included within the spirit and purview of this application.

All patents, patent applications, provisional applications, and publications referred to or cited herein are incorporated by reference in their entirety, including all figures and tables, to the extent they are not inconsistent with the explicit teachings of this specification.

We claim:
1. An isolated compound having, the following formula:

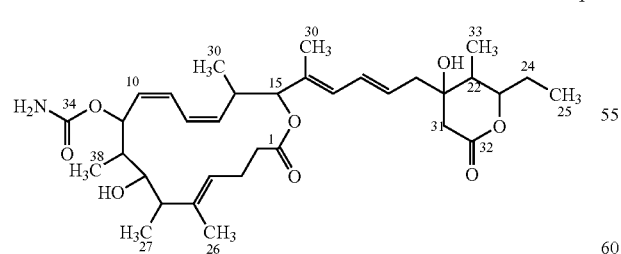

or a salt thereof,
wherein the compound has the following spectral data:
$^{13}$C NMR (d4-methanol, 150 MHz): 173.9(C), 173.6(C), 160.0(C), 138.0(CH), 137.7(C), 133.4(C), 131.47(CH), 131.1(CH), 130.8(CH), 130.2(CH), 126.4(CH broad), 126.4(CH broad), 125.8(CH), 85.6(CH), 84.4(CH), 80.3 (CH broad), 72.7(C), 69.7(CH broad), 49.4(CH (hidden)), 44.6(CH), 43.2(CH2), 40.8(CH broad), 39.4(CH2), 35.7(CH), 34.6(CH2), 27.9(CH2), 23.0(CH2), 16.9(CH3), 16.9(CH3), 12.9(CH3), 11.9(CH3), 11.5(CH3), 11.5(CH3), 9.4(CH3);

$^{1}$H NMR(d4-methanol, 600 MHz): 6.58(dd 11.3, 11.3), 6.36(dd 12.3. 11.7), 6.35(dd 11.0, 11.0), 6.07(d 10.3), 5.84(bd 13.7), 5.81(ddd 15.2, 8.1, 6.2), 5.51(dd 10.3, 10.3), 5.28(dd 10.3, 10.3), 5.1(dd 6.9, 6.9), 5.05(d 10.3), 4.01(ddd 10.3, 7.6, 2.8), 3.31(bm), 3.03(bm), 2.72(d 17.2), 2.43(dd 14.5, 3), 2.42(bs), 2.33(m), 2.31(d 17.2), 2.22(m), 2.19(dd 14.5, 11.7), 2.03(m), 1.85(dq 9.6, 7.6), 1.84(m), 1.78(s), 1.72(bq 6.8), 1.61(ddt 14.4, 6.8, 6.8), 1.44(bs), 1.1(d 6.5), 1.08(d 7.2), 1.02(d 6.9), 1.00(t 7.4), 0.86(d 6.7).

2. A method for inhibiting proliferation of cancer cells, said method comprising administering, to a patient in need of such treatment, an effective amount of a compound having the following structure:

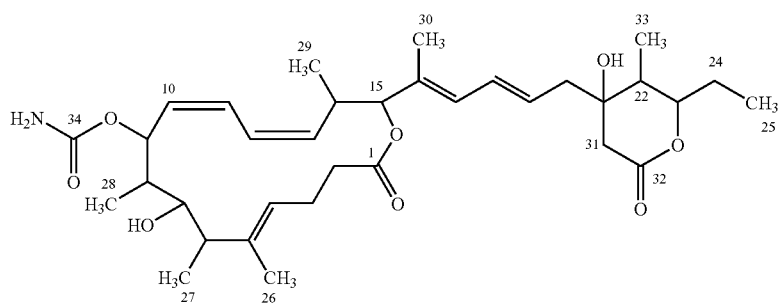

or a salt thereof;
wherein said compound has the following spectral data:
$^{13}$C NMR (d4-methanol, 150 MHz): 173.9(C), 173.6(C), 160.0(C), 138.0(CH), 137.7(C), 133.4(C), 131.47(CH), 131.1(CH), 130.8(CH), 130.2(CH), 126.4(CH broad), 126.4(CH broad), 125.8(CH), 85.6(CH), 84.4(CH), 80.3 (CH broad), 72.7(C), 69.7(CH broad), 49.4(CH (hidden)), 44.6(CH), 43.2(CH2), 40.8(CH broad), 39.4(CH2), 35.7(CH), 34.6(CH2), 27.9(CH2), 23.0(CH2), 16.9(CH3), 16.9(CH3), 12.9(CH3), 11.9(CH3), 11.5(CH3), 11.5(CH3), 9.4(CH3);

$^{1}$H NMR(d4-methanol, 600 MHz): 6.58(dd 11.3, 11.3), 6.36(dd 12.3. 11.7), 6.35(dd 11.0, 11.0), 6.07(d 10.3), 5.84(bd 13.7), 5.81(ddd 15.2, 8.1, 6.2), 5.51(dd 10.3, 10.3), 5.28(dd 10.3, 10.3), 5.1(dd 6.9, 6.9), 5.05(d 10.3), 4.01(ddd 10.3, 7.6, 2.8), 3.31(bm), 3.03(bm), 2.72(d 17.2), 2.43(dd 14.5, 3), 2.42(bs), 2.33(m), 2.31(d 17.2), 2.22(m), 2.19(dd 14.5, 11.7), 2.03(m), 1.85(dq 9.6, 7.6), 1.84(m), 1.78(s), 1.72(bq 6.8), 1.61(ddt 14.4, 6.8, 6.8), 1.44(bs), 1.1(d 6.5), 1.08(d 7.2), 1.02(d 6.9), 1.00(t 7.4), 0.86(d 6.7), wherein said cancer cells are selected from the group consisting of breast, lung, ovarian and pancreatic cancer cells.

3. A pharmaceutical composition comprising a compound having the following structure:

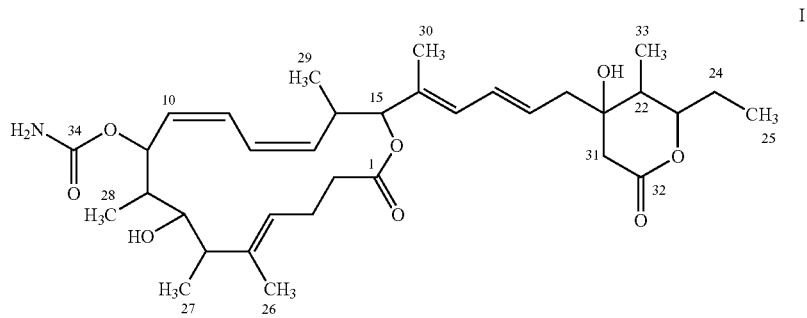

or a salt thereof, wherein the compound has the following spectral data:

$^{13}$C NMR (d4-methanol, 150 MHz): 173.9(C), 173.6(C), 160.0(C), 138.0(CH), 137.7(C), 133.4(C), 131.47(CH), 131.1(CH), 130.8(CH), 130.2(CH), 126.4(CH broad), 126.4(CH broad), 125.8(CH), 85.6(CH), 84.4(CH), 80.3 (CH broad), 72.7(C), 69.7(CH broad), 49.4(CH (hidden)), 44.6(CH), 43.2(CH2), 40.8(CH broad), 39.4(CH2), 35.7(CH), 34.6(CH2), 27.9(CH2), 23.0(CH2), 16.9(CH3), 16.9(CH3), 12.9(CH3), 11.9(CH3), 11.5(CH3), 11.5(CH3), 9.4(CH3), $^1$H NMR(d4-methanol, 600 MHz): 6.58(dd 11.3, 11.3), 6.36(dd 12.3. 11.7), 6.35(dd 11.0, 11.0), 6.07(d 10.3), 5.84(bd 13.7), 5.81(ddd 15.2, 8.1, 6.2), 5.51(dd 10.3, 10.3), 5.28(dd 10.3, 10.3), 5.1(dd 6.9, 6.9), 5.05(d 10.3), 4.01(ddd 10.3, 7.6, 2.8), 3.31(bm), 3.03(bm), 2.72(d 17.2), 2.43(dd 14.5, 3), 2.42(bs), 2.33(m), 2.31(d 17.2), 2.22(m), 2.19(dd 14.5, 11.7), 2.03(m), 1.85(dq 9.6, 7.6), 1.84(m), 1.78(s), 1.72(bq 6.8), 1.61(ddt 14.4, 6.8, 6.8), 1.44(bs), 1.1(d 6.5), 1.08(d 7.2), 1.02(d 6.9), 1.00(t 7.4), 0.86(d 6.7).

* * * * *

UNITED STATES PATENT AND TRADEMARK OFFICE
CERTIFICATE OF CORRECTION

PATENT NO. : 7,626,043 B2
APPLICATION NO. : 11/890686
DATED : December 1, 2009
INVENTOR(S) : Wright et al.

It is certified that error appears in the above-identified patent and that said Letters Patent is hereby corrected as shown below:

Column 2
Line 55
"$R_1$=—H," should read --$R_1$= - H,--.

Line 56
"$R_1$=—H," should read --$R_1$= - H,--.

Line 57
"$R_1$=—H," should read --$R_1$= - H,--.

Line 63
"Y=—H," should read --Y= - H,--.

Column 4
Line 56
"$R_1$=—H," should read --$R_1$= -H,--.

Line 57
"$R_2$=—H," should read --$R_2$= -H,--.

Line 58
"$R_3$=—H," should read --$R_3$= -H,--.

Line 63
"Y=—H," should read --Y= - H,--.

CERTIFICATE OF CORRECTION (continued)
U.S. Pat. No. 7,626,043 B2

Column 13
Claim 1

"

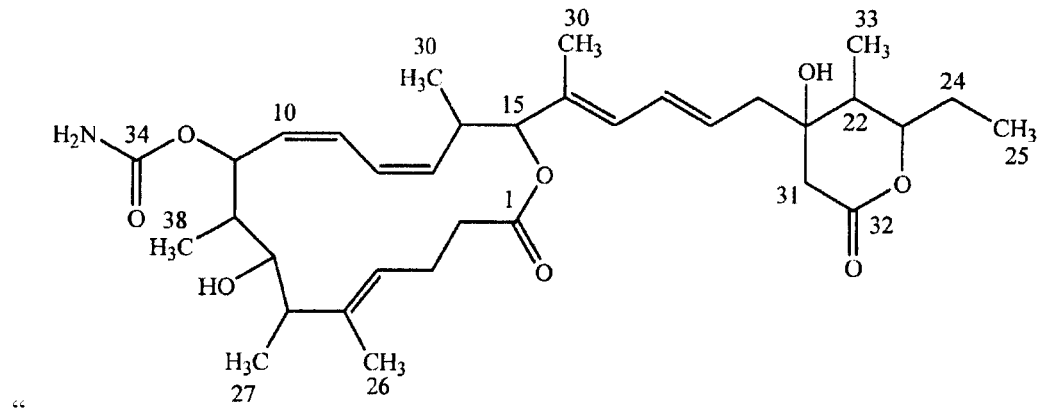

"

should read

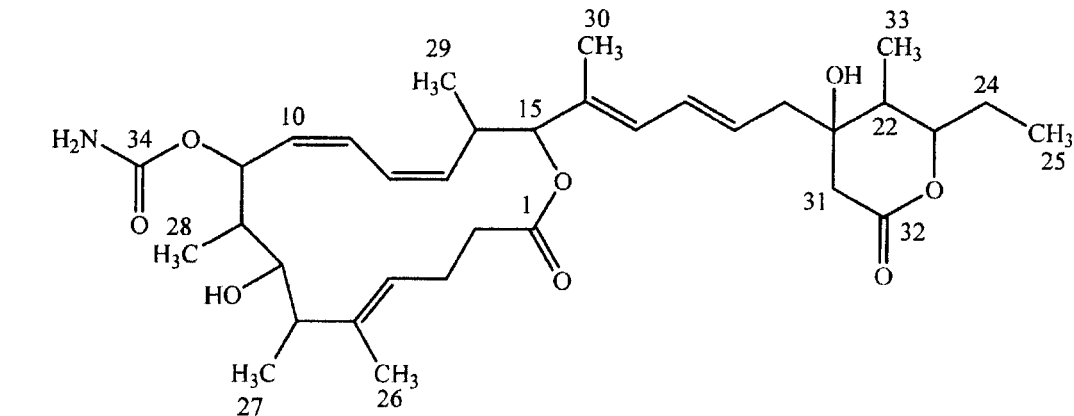

--                                                                                                                                      --.

Signed and Sealed this

Sixteenth Day of March, 2010

David J. Kappos
*Director of the United States Patent and Trademark Office*